US012502493B2

(12) United States Patent
Bartels et al.

(10) Patent No.: US 12,502,493 B2
(45) Date of Patent: *Dec. 23, 2025

(54) BLOCKING DEVICE

(71) Applicant: INVOX BELGIUM NV, Diepenbeek (BE)

(72) Inventors: Frank Bartels, Hattingen (DE); Juergen Rawert, Cologne (DE)

(73) Assignee: INVOX BELGIUM NV, Diepenbeek (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/337,453

(22) Filed: Jun. 20, 2023

(65) Prior Publication Data

US 2024/0024593 A1 Jan. 25, 2024

Related U.S. Application Data

(63) Continuation of application No. 16/955,794, filed as application No. PCT/EP2018/086834 on Dec. 22, 2018, now Pat. No. 11,717,622.

(Continued)

(30) Foreign Application Priority Data

Dec. 22, 2017 (EP) .................................... 17210392

(51) Int. Cl.
*A61M 15/00* (2006.01)

(52) U.S. Cl.
CPC ...... *A61M 15/0081* (2014.02); *A61M 15/009* (2013.01); *A61M 2202/04* (2013.01);

(Continued)

(58) Field of Classification Search
CPC .............. A61M 15/00; A61M 2202/04; A61M 2205/276; A61M 2205/8281;

(Continued)

(56) References Cited

U.S. PATENT DOCUMENTS 11,717,622 B2 * 8/2023 Bartels ................ A61M 15/009
128/200.23

* cited by examiner

*Primary Examiner* — Vishal Pancholi
(74) *Attorney, Agent, or Firm* — Synergy IP Group AG

(57) ABSTRACT

The inhalation device for medically active liquids (F) for generation of an aerosol comprises a housing (1), a reservoir (2), a pumping device with a pumping chamber (3), and a nozzle (6), wherein the interior volume of the pumping chamber (3) is changeable by means of linear relative motion of the pumping chamber to the riser pipe (5). Said linear relative motion can be effected by a relative rotation of a rotatable part (1A) which is part of, or connected to, the housing (1) with respect to a second part (1B) of said housing (1), in that said relative rotation can be transferred by means of a gear mechanism into said relative translational motion. A means for the storage of potential energy (7) is provided which is chargeable by means of said relative rotation, and wherein said energy is releasable to said pumping device when released by activation of a release means. A blocking device is provided which is adapted to block activation of the release means and/or release of the means for the storage of potential energy (7) during rotation of the rotatable part (1A) and/or during loading of the means for the storage of potential energy (7). Also, a method for the prevention of undesired emission of medically active liquid or aerosol from an inhalation device is disclosed.

20 Claims, 3 Drawing Sheets

Related U.S. Application Data

(60) Provisional application No. 62/610,058, filed on Dec. 22, 2017.

(52) U.S. Cl.
CPC ................. *A61M 2205/276* (2013.01); *A61M 2205/8281* (2013.01)

(58) Field of Classification Search
CPC ............ A61M 15/009; A61M 15/0081; A61M 11/00; B05B 11/3091
See application file for complete search history.

BLOCKING DEVICE

CROSS REFERENCE TO RELATED APPLICATIONS

This application is a continuation of U.S. application Ser. No. 16/955,794, now U.S. Pat. No. 11,717,622 B2, which is a U.S. National Stage Application filed under 35 U.S.C. § 371 claiming the benefit of PCT Application No. PCT/EP2018/086834, filed on Dec. 22, 2018, which claims priority to and the benefit of European Application No. 17210392.1, filed on Dec. 22, 2017, and U.S. Provisional Application Ser. No. 62/610,058, filed on Dec. 22, 2017, all of which are hereby incorporated herein by reference in their entireties.

FIELD OF THE INVENTION

The invention relates to the field of inhalation devices for liquids. In particular, the invention relates to a blocking device for such an inhalation device.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle.

The inhalation device further comprises a tension or pressure spring, serving as a means for the storage of potential energy. By manual rotation of a part of the housing, said means is loaded. This is achieved in that the rotational motion is transferred by a gear mechanism into a translational motion. The translational motion loads the spring. Both motions come to an end when the loading is completed. The means for the storage of potential energy is kept in this loaded state until it is released, e.g. by manually pushing a release button. Upon release, the energy stored in the spring is used to generate a pressure within the pumping unit. The pressurized liquid is released through the nozzle, producing the aerosol, while the aforesaid linear motion is reversed. When said reversed linear motion reaches its end position, the pressure abates, the aerosol generation ends, and the device must be loaded again by means of another rotation in order to generate another dose of aerosol.

It is important to ensure that an inhalation device is used correctly by the user or patient. To address this need, various blocking mechanisms have been suggested which have been designed to block certain device manipulations by the user which are incorrect and which could be detrimental for the user.

For example, US2015/0040890 describes a soft mist inhaler with a blocking mechanism that prevents the premature loading of a spring which stores potential energy by rotation of a rotatable part before the device is fully assembled: The rotation is blocked until a detachable part is connected to the housing and the housing is completely closed (claim 1, claim 15). Similarly, US20130206136 describes an inhaler with a mechanism that prevents the operation of the device or its loading by rotating a rotatable part without first assembling the device completely.

US2015/0320948 and DE10239443 (A1) disclose blocking mechanisms which block the further operation of an inhalation device after its designated life time (or after the designated life time of a cartridge inside the inhalation device). In other words, after the user or patient has performed a predefined number of device actuations to receive said predefined number of doses, the device blocks further attempts to load the device and release a further dose of aerosol, regardless of whether or not residual amounts of liquid are still present in the liquid reservoir.

However, there is still a need for inhalation devices which exhibit improved blocking mechanisms which also prevent incorrect or undesirable manipulations by the user or patient during the life time of the inhaler, i.e. at other points of time during the repeated use of the device. For example, it is desirable to prevent the user from performing—or attempting to perform—more than one loading action in sequence without releasing any aerosol. This could lead to subsequent malfunction of the inhalation device. Moreover, if the device comprises a dose counter, it is likely that each loading cycle will be counted as a dosing, even though no dose was released to the patient or user. As a consequence, the inhaler (or the cartridge inside the inhaler) will not last for the entire period of time over which the prescribing physician intended to treat the respective patient.

It is also desirable at any time during the regular use of the inhalation device to prevent the premature actuation of the release button. If the release button is pressed during performing the loading of the device, the loading motion can result in an undesired immediate emission of material through the nozzle, or in an unintended emission immediately at the end of the loading. Depending on the atomization mechanism, if the pressure is not sufficient for aerosol production (atomization), no aerosol, but liquid may emitted. Therefore, aerosol or liquid can spill and contaminate objects or persons, which is undesired. Also, spilled liquid is no more available for its intended purpose. The liquid may contain active ingredients; thus, bystanders might be harmed by spilled liquid.

OBJECT OF THE INVENTION

The object of the invention is the provision of a device that comprises an improved mechanism for the prevention of incorrect use of the device during the time span of regular use, and which avoids or overcomes at least one of the drawbacks of the known art.

DESCRIPTION OF THE INVENTION

The object is solved by a device according to claim 1, as well as a method according to claim 10. Advantageous embodiments are described in the respective dependent claims, the subsequent description, as well as the accompanying figures.

In particular, the invention provides an inhalation device for medically active liquids (F) for generation of an aerosol, comprising a housing (1), inside this housing (1) a reservoir (2) for storing a liquid (F), a pumping device with a pumping chamber (3) for generation of a pressure inside said pumping chamber (3), wherein the pumping chamber (3) is fluidically connected with the reservoir (2), a riser pipe (5) which can be received with at least one reservoir-facing, interior end (5A) in said pumping chamber (3), and a nozzle (6) which is connected liquid-tight to an exterior end (5B) of the riser pipe (5), wherein the interior volume of the pumping chamber (3) is changeable by means of linear relative motion of the pumping chamber to the riser pipe (5). Said linear relative motion can be effected by a relative rotation of a rotatable part (1A) which is part of, or connected to, the housing (1) with respect to a second part (1B) of said housing (1), such that said relative rotation is converted into said linear relative motion by means of a gear mechanism. The inhalation device further comprises a means for the storage of potential energy (7) which is chargeable by means of said relative rotation, and wherein said energy is releasable to said pumping device when released by activation of a release means. Moreover, the inhalation device comprises a blocking device (9) which is adapted to block rotation of the rotatable part (1A). This embodiment is further characterised in that the blocking device (9) is adapted to be moveable between a blocking position and a non-blocking position, and in that the blocking device is adapted to (a) move into the blocking position upon rotating the rotatable part (1A) by a predefined rotation angle, and (b) move into the non-blocking position upon activating the release means.

The inhalation device preferably represents an inhaler from the class of so-called soft mist inhalers. Its pumping device (or pumping unit) serves for generation of a pressure inside the pumping chamber. The pumping chamber is fluidically connected with the at least one reservoir. A riser pipe which can be received with at least one reservoir-facing, interior end in said pumping chamber, serves for transporting the liquid from the reservoir to the pumping chamber. A nozzle which is connected liquid-tight to an exterior end of the riser pipe, servers for generation of the inhalable mist of fine liquid droplets. In the case of a soft mist inhaler, the nozzle is of the impingment type. Typically, the interior volume of the pumping chamber is changeable by means of linear relative motion of the pumping chamber to the riser pipe.

For a soft mist inhaler, a rather high pressure is needed for aerosol droplet generation. The typical force that a person can exert by e.g. pressing onto said chamber is too low. Thus, said linear relative motion is achieved by a relative rotation of a rotatable part which is part of, or connected to, the housing with respect to a second part of said housing, and wherein the rotatable part and the second part are arranged such that said relative rotation is converted into said linear relative motion by means of a gear mechanism. In other words, the housing comprises two separate parts, and when holding these parts in different hands and rotating one of these parts relative to the other, a gear mechanism will convert the relative rotation into a linear motion which is used to build up a sufficiently high pressure in the pumping chamber.

In order to produce a uniform mist, the pressure needs to be rather uniform as well during the time it is present. Since a person is not always capable of reproducibly provide such a uniform pressure by uniformly rotating the rotatable part of the housing, resulting in varying droplet sizes and emission times, a means for the (intermediate) storage of potential energy is provided which is chargeable by means of said relative rotation, wherein said energy is releasable to said pumping device when released by activation of a release means. In other words, in order to eliminate the influence of the person which uses the inhalation device on droplet formation, the person is only used for loading a means for storage of potential energy, such as a pressure or tension spring, by rotating the rotatable part relative to the second part, or vice-versa. After said (manual) loading is complete, a release means such as a button is activated, and the means for storage of potential energy releases its energy in form of a constant pressure to the pressure chamber. Thus, a uniform and reproducible generation of droplets becomes possible.

According to the invention, the inhalation device comprises a blocking mechanism which can block the rotation of the rotatable part. The blocking device is adapted to be moveable between a first position (also referred to as blocking position) and a second position (also referred to as non-blocking position). Preferably, the blocking position and the non-blocking position are axial positions, meaning that the movement between these two positions is an axial movement.

This means that the blocking device is able to take a first position which is, with respect to the tip (or the bottom) of the inhalation device, further away from (or closer to) said tip (or bottom) than in a second position. This definition is particularly useful when the device has a distinct longitudinal axis, which is the case if the inhalation device has a longitudinal, e.g. cylindrical, shape. Another definition makes use of the rotation axis of the rotatable part; the two axial positions are along different locations of an axis which is parallel to said rotational axis. Thus, the latter definition is also usable for e.g. a spherical (ball shaped) inhalation device.

Moreover, the blocking device is designed to perform this movement repeatedly during the regular use or life time of the inhalation device, or over the use of a cartridge of liquid within the device. In particular, it is adapted to perform at least one movement from the first to the second position and at least one movement back from the second to the first position within each dosing event, also referred to as dosing cycle, which comprises the charging of the device and the release of a dose of aerosol to the user or patient.

According to one embodiment, the blocking device is radially immobile. This means that the blocking device is unable to rotate relative to the second part which is part of, or connected to, the housing. At the same time, the rotatable part is capable of rotating relative to the blocking device. This allows for a construction wherein the blocking device can selectively block rotation of the rotatable part.

In one embodiment, the blocking device, upon activation of the release means, can be pushed from the first position, or blocking position, to the second position, or non-blocking position, by means of a catch which is directly or indirectly fixed to the pumping chamber, such that it moves together with the movement of the pumping chamber, preferably also in an axial direction. In other words, when the pumping chamber, upon activation of the release means (e.g. by pushing a release button), moves axially such as to decrease its interior volume and to increase its internal pressure, the catch which is directly or indirectly affixed to the chamber performs the same axial motion, pushing the blocking device from the blocking position to the non-blocking position.

In another embodiment, the rotatable part has an axial recess configured to receive at least a part of the blocking device. Optionally, the recess is configured and dimensioned such that, when said blocking device is at least partially received in said recess, the rotation of the rotatable part is blocked or nearly blocked, whereas when the blocking device is outside of said recess, the rotatable part is unblocked. As used herein, the expression "nearly blocked" means that a minor rotational movement of the rotatable part is still possible even when the blocking device is positioned in the recess.

According to this embodiment, the first position, or blocking position, of the blocking device is its position wherein it is at least partially received by, or within, the recess, whereas in its second position, or non-blocking position, it is entirely outside of the recess.

Such a recess is easy to manufacture, and it is also particularly advantageous in that a blocking device held in a recess allows the provision of a particularly strong mechanical blocking mechanism. In fact, it is easy to design such blocking mechanism to be strong enough to withstand all manual force that may be applied in the course of an erroneous use by a patient; essentially, the user or patient would have to destroy the inhalation device in order to overcome the blocking mechanism.

Optionally, the recess is larger than the blocking device such as to allow a restricted further rotation of the rotatable part upon the receipt of the blocking device in the recess before rotation of the rotatable part is entirely blocked. In this context, the expression "larger" means the dimension of the recess in a horizontal direction, or perhaps more precisely, the circumferential dimension, and the corresponding dimension of the blocking device or the part of the blocking device which is in its blocking position received in the recess. If such size difference is present, the rotation of the rotatable part may reach a first predetermined angle at which the blocking device can be received in the recess, but due to the size of the recess, the rotation may then be continued for a relatively small rotation angle until the blocking device entirely blocks any further rotation. Such small or restricted rotation movement while the blocking device is already in the blocking position within the recess should preferably be less than about 15°; more preferably, the rotation angle of this restricted rotation is not more than about 10°, such as between 5° and 10°.

In one embodiment, the aforementioned catch is configured to fit in the recess. In this case, it is further preferred that the catch is also axially moveable within the recess. After the dose is delivered, the catch pushes the blocking device out of the recess, now allowing for rotation of the rotatable part. All regions along the circumference of the rotatable part except said recess allow for the blocking device to slide over these as long as the blocking device is in its second or non-blocking position. At the predetermined rotation angle of e.g. 180 degrees (optionally minus the rotation angle of the restricted rotation allowed by a recess that is larger than the blocking device), the blocking device "falls" back from the circumference into the recess, thus blocking further rotation.

In one embodiment, said catch is configured to fit in, as well as to axially move within, but not to leave, said recess. In this embodiment, it is particularly assured that the blocking device can leave the recess, while keeping the necessary linear motion of the catch to a minimum. To ensure that the blocking device is actually pushed over the edge of the recess, it is clear that the respectively positioned edge of the catch must align with, or slightly project above, the circumference of the rotatable part along which the blocking device can slide when being in the second position.

In another embodiment, not even the catch edge projects above the circumference; in order to nevertheless allow the blocking device to leave the recess, a chamfer or the like can be provided that allows sliding out of the recess upon rotating the rotatable part which is part of, or connected to, the housing.

In a further preferred embodiment of the inhalation device, the axial movement of the blocking device from the non-blocking position into its blocking position may be facilitated by the pressure exerted e.g. by compression spring or the like.

In yet another preferred embodiment, the inhalation device comprises a rotatable part with two recesses. Preferably, the two recesses have approximately the same dimensions, and they are preferably positioned apart from each other by a rotation angle of about 180°.

The inhalation device of the invention may further comprise a second blocking device which, in contrast to the above-described blocking device, is adapted to block the activation of the release means such as to prevent the release of stored potential energy from the means for storing potential energy during the rotation of the rotatable part. Preferably, such second blocking device is adapted to block the activation of the release means at all rotation angles except at the predetermined rotation angle at which the previously described blocking device ("first blocking device") is in its blocking position. Thus it is ensured that the release of aerosolised liquid occurs only when the device has been fully charged; premature emission of aerosol or even non-aerosolised liquid cannot occur.

Optionally, the second blocking device may also include a member which is moveable between a blocking position and a non-blocking position. Such movement between these two positions may be axial, radial, rotational or circumferential. In one of the preferred embodiments, the movement from the blocking position to the non-blocking position is a rotational or circumferential movement, i.e. the non-blocking position is radially and optionally also axially the same as the blocking position, but the positions differ by an angle of rotation.

The combined effects of the two blocking devices as described above would render the repeated regular use of the inhalation device safe and reliable, prevent the inadvertent emission of liquid or aerosol and ensure that the inhalation device will have its designated use time. More specifically, the respective blocking devices could be adapted such that, within each dosing cycle, the user or patient initially performs a rotation movement such as to rate the rotatable part relative to the second part of the housing of the inhaler. During this rotation, the first blocking device is in its non-blocking position (such as to allow the rotation), while the second blocking device is in its blocking position, until a predetermined angle of rotations, such as 170° to 180°, has been reached. At this point, the first blocking device moves into its blocking position (optionally pushed into a recess by a spring) such as to block the further rotational movement (optionally with the exception of a minor rotation of a few degrees, as previously described). In this position in which the further rotation of the rotatable part is blocked, the second blocking device is in the non-blocked position.

The invention relates also to a method for the prevention of undesired emission of medically active liquid or aerosol from an inhalation device. Preferably, the method is used with an inhalation device of the aforesaid type, having some or all of the aforesaid features. However, the method can also be used on other inhalation devices as well which, according to the state of the art, do not inhibit parallel actuation (emission of droplets) and (re-)loading.

In order to avoid repetitions, reference is made to the above description.

It is preferred that the aforementioned blocking device is also part of the inhalation device. It is further preferred that the blocking device moves from a first position in which it blocks the rotation of the rotatable part to a second position in which it unblocks rotation of said rotatable part. It is also preferred that, after rotating the rotatable part for a predefined angle of e.g. 180 degrees, thus reloading the inhalation device for another dose, the blocking device moves back from the second position to the first position.

It is also preferred that, for activation of the release means and/or release of the means for the storage of potential, a catch is provided that slides along an axial recess which is formed in the rotatable part, pushing the blocking device from said first position to said second position. Once again, with regard to these steps, reference is made to the above description in order to avoid repetitions.

Moreover, the invention provides the following specific embodiments:

(E1) An inhalation device for medically active liquids (F) for generation of an aerosol, comprising a housing (1), inside this housing (1) a reservoir (2) for storing a liquid (F), a pumping device with a pumping chamber (3) for generation of a pressure inside said pumping chamber (3), wherein the pumping chamber (3) is fluidically connected with the reservoir (2), a riser pipe (5) which can be received with at least one reservoir-facing, interior end (5A) in said pumping chamber (3), and a nozzle (6) which is connected liquid-tight to an exterior end (5B) of the riser pipe (5), wherein the interior volume of the pumping chamber (3) is changeable by means of linear relative motion of the pumping chamber to the riser pipe (5), and wherein said linear relative motion can be effected by a relative rotation of a rotatable part (1A) which is part of, or connected to, the housing (1) with respect to a second part (1B) of said housing (1), such that said relative rotation is converted into said linear relative motion by means of a gear mechanism, and wherein a means for the storage of potential energy (7) is provided which is chargeable by means of said relative rotation, and wherein said energy is releasable to said pumping device when released by activation of a release means, characterized in that a blocking device (9) is provided which is adapted to block the activation of the release means and/or release of the means for the storage of potential energy (7) during rotation of the rotatable part (1A) and/or during loading of the means for the storage of potential energy (7); and/or a blocking device (9) is provided which is adapted to block loading of the means for the storage of potential energy (7) and/or rotation of the rotatable part (1A) when the release means is activated.

(E2) The inhalation device according to embodiment E1, wherein the blocking device (9) is radially immobile.

(E3) The inhalation device according to embodiment E1 or E2, wherein in a first position, the blocking device (9) blocks rotation of the rotatable part (1A), while in a second position, the blocking device (9) does not block said rotatable part (1A).

(E4) The inhalation device according to embodiment E3, wherein said first and second position are axial positions.

(E5) The inhalation device according to embodiments E3 or E4, wherein the blocking device (9), upon activation of the release means, can be pushed from the first position to the second position by a catch (10) which is fixed to and/or can move together with the pumping chamber (3).

(E6) The inhalation device according to any of embodiments E3 to E5, wherein the blocking device (9) is adapted to, after rotation of the rotatable part (1A) for a predefined rotation angle, automatically moves back into the first position, thus blocking further rotation of the rotatable part (1A).

(E7) The inhalation device according to any of the embodiments E1 to E6, wherein the rotatable part (1A) has an axial recess (11) configured to receive at least a part of the radially immobile blocking device (9) such that, when said blocking device (9) is at least partially received in said recess (11), rotation of the rotatable part (1A) is blocked, whereas when the blocking device (9) is outside of said recess (11), the rotatable part (1A) is unblocked.

(E8) The inhalation device according to embodiments E5 and E7, wherein said catch (10) is configured (i) to fit in, and (ii) to axially move within said recess (11).

(E9) The inhalation device according to any of the embodiments E1 to E8, wherein said device comprises two recesses (11).

(E10) A method for the prevention of undesired emission of medically active liquid or aerosol from an inhalation device, the inhalation device comprising a housing (1), inside this housing (1) a reservoir (2) for storing a liquid (F), a pumping device with a pumping chamber (3) for generation of a pressure inside said pumping chamber (3), wherein the pumping chamber (3) is fluidically connected with the reservoir (2), a riser pipe (5) which can be received with at least one reservoir-facing, interior end (5A) in said pumping chamber (3), and a nozzle (6) which is connected liquid-tight to an exterior end (5B) of the riser pipe (5), wherein the interior volume of the pumping chamber (3) is changeable by means of linear relative motion of the pumping chamber to the riser pipe (5), wherein said linear relative motion is effected by a relative rotation of a rotatable part (1A) which is part of or connected to the housing (1) with respect to a second part (1B) of said housing (1), and wherein a means for the storage of potential energy (7) is provided which is loaded by means of said relative rotation, and which releases said energy to said pumping mechanism when released by activating a release means, characterized in that (i) activating of the release means and/or release of the means for the storage of potential energy (7) during rotating the rotatable part (1A), or during loading of the means for the storage of potential energy (7), is blocked, and/or (ii) loading of the means for the storage of potential energy (7) and/or rotating the rotatable part (1A) is blocked when the release means is activated.

(E11) The method according to embodiment E10, wherein for said blocking, a blocking device is provided.

(E12) The method according to embodiment E11, wherein the blocking device moves from a first position in which it blocks the rotation of the rotatable part (1A) to a second position in which it unblocks rotation of said rotatable part (1A).

(E13) The method according to embodiments E11 and E12, wherein, after rotating the rotatable part (1A) for a predefined angle, thus reloading the inhalation device for another dose, the blocking device moves back from the second position to the first position.

(E14) The method according to embodiments E12 or E13, wherein, for activation of the release means and/or release of the means for the storage of potential energy, a catch is provided that slides along an axial recess which is formed in the rotatable part (1A), pushing the blocking device from said first position to said second position.

DESCRIPTION OF FIGURES

In FIG. 1, a schematic cut view of an inhalation device is shown.

Figure 1:
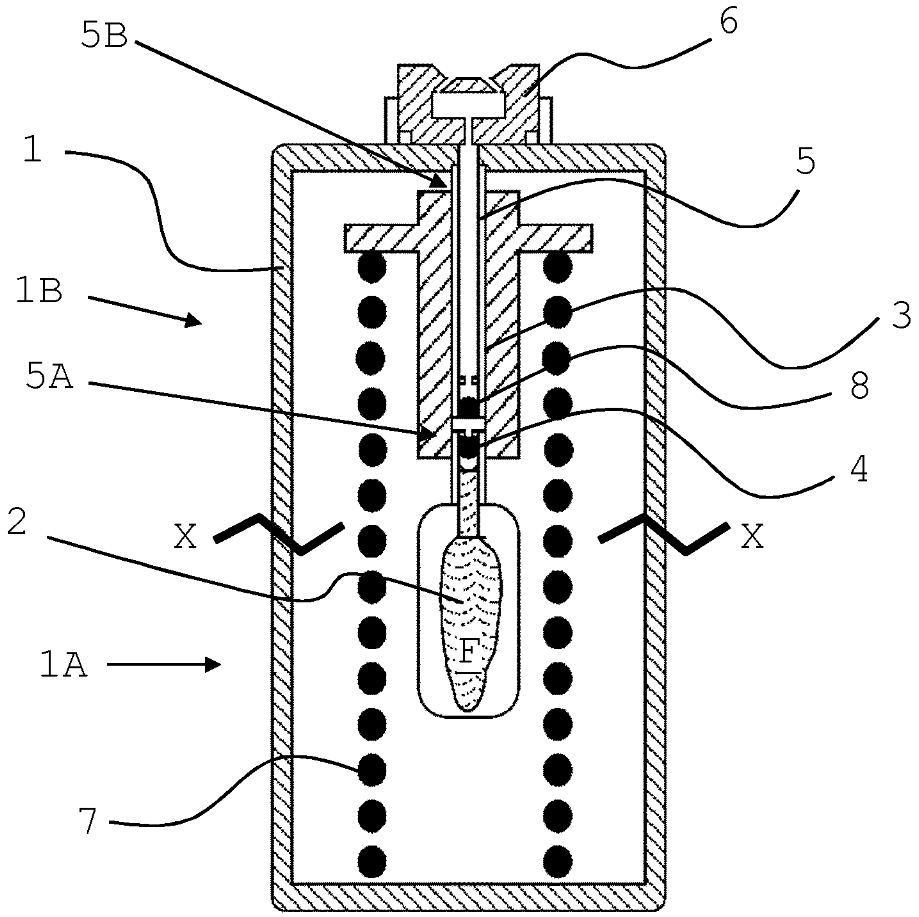
FIG. 1 shows a schematic view of some components of an inhalation device.

The inhalation device comprises a housing 1, inside this housing 1 a reservoir 2 for storing a liquid F, and a pumping device with a pumping chamber 3 for generation of a pressure inside said pumping chamber 3. The pumping chamber 3 is fluidically connected with the reservoir 2. The device further comprises a riser pipe 5 which can be received with at least one reservoir-facing, interior end 5A in said pumping chamber 3, and a nozzle 6 which is connected liquid-tight to an exterior end 5B of the riser pipe 5. The interior volume of the pumping chamber 3 is changeable by means of linear relative motion of the pumping chamber to the riser pipe 5. Further, valves 4, 8 are present in order to keep liquid F from flowing contrary to the desired flow direction, i.e. towards nozzle 6. Along the break lines X, housing 1 is divided in a rotatable part 1A and a second part 1B.

Said linear relative motion can be effected by a relative rotation of rotatable part 1A with respect to second part 1B. The relative rotation can be transferred by means of a gear mechanism (not shown) into said relative translational motion.

Further, a means for the storage of potential energy 7 is provided which is chargeable by means of said relative rotation, and said energy is releasable to said pumping device when released by activation of a release means (not shown).

Figure 2:
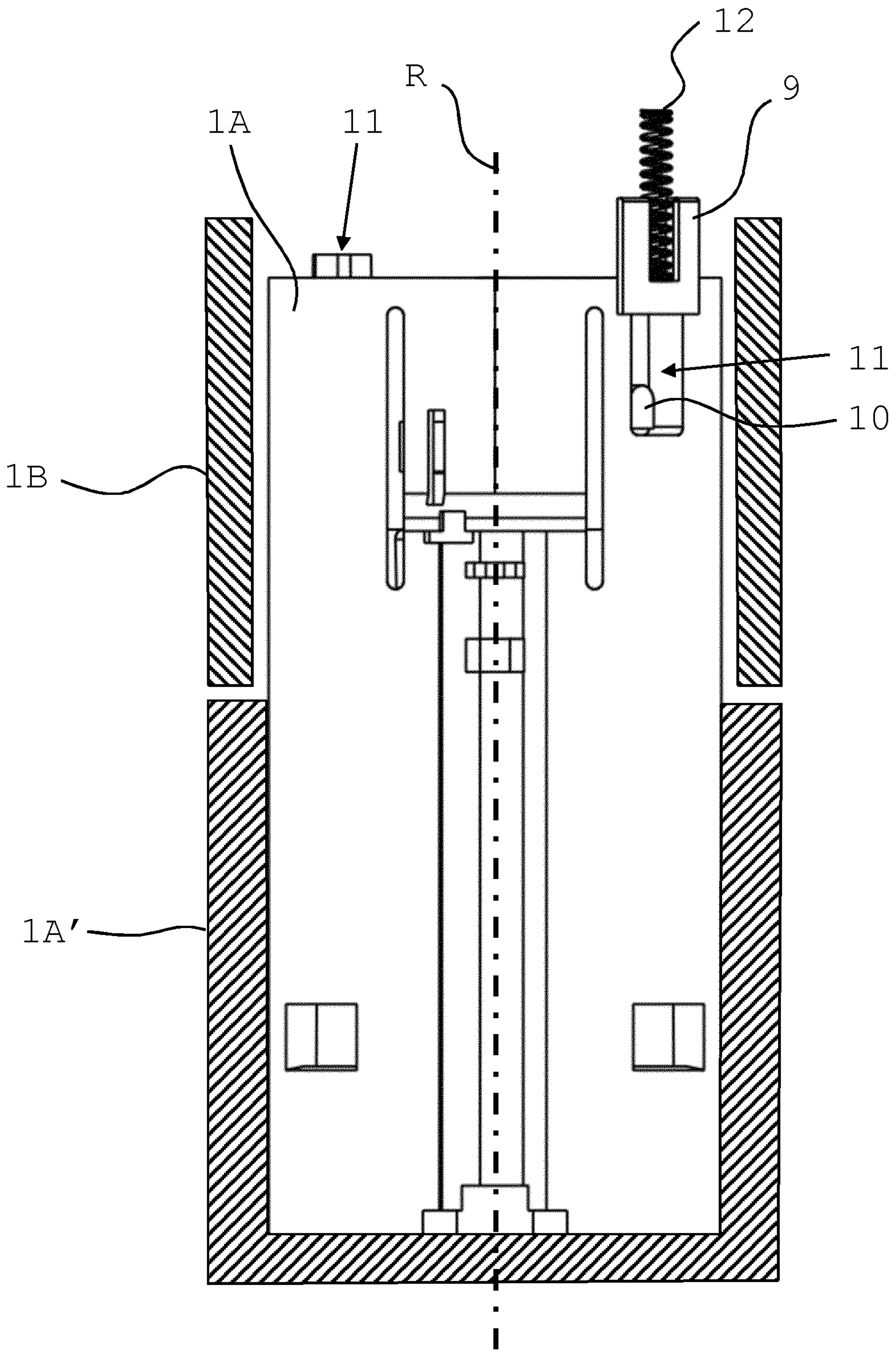
FIG. 2 shows a side view of one embodiment of the invention.

In FIG. 2, a side view of some components of one embodiment of the invention is shown. For the sake of clarity, most components of the inhalation device which have are already been introduced are omitted.

In this embodiment, rotatable part 1A is connected to a co-rotatable part 1A' of the housing. Both parts 1A, 1A' are connected in a way such that when the co-rotatable (or "according") part 1A' is rotated, rotatable part 1A rotates as well. Thus, from a constructional point of view, rotatable part 1A can be regarded as being a part of the housing 1. Schematically, the second part 1B is also depicted. The gap between the inner wall of second part 1B and rotatable part 1A indicates that the second part 1B is configured to not co-rotate with rotatable part 1A (and co-rotatable part 1A').

At the upstream side of the rotatable part 1A (top of the figure), blocking device 9 is depicted. Said blocking device 9 is radially immobile, but axially mobile (vertical direction in the figure). Thus, it cannot rotate together with rotatable part 1A around a rotation axis R. As shown in FIG. 2, in a first position, the blocking device 9 blocks rotation of the rotatable part 1A, while in a second position (not shown), blocking device 9 does not block said rotatable part 1A. In the depicted embodiment, both positions are axial positions.

As can be seen, rotatable part 1A has an axial recess 11 configured to receive the radially immobile blocking device 9 such that, when said blocking device 9 is at least partially received in said recess 11, rotation of the rotatable part 1A is mechanically blocked, whereas when the blocking device 9 is outside of said recess 11, the rotatable part 1A is unblocked and can rotate relative to the second part 1B.

Further, a catch 10 is present which can move together with the pumping chamber (not shown). It is recalled that an axial motion of the pumping chamber results in pressure generation. Thus, upon activation of the release means (not shown), blocking device 9 is pushed from the first position to the second position by said catch 10. Catch 10 is configured to fit in, and to axially move within, said recess 11.

Also, the blocking device 9 is adapted to, after rotation of the rotatable part 1A for a predefined rotation angle (such as 180 degrees), automatically move back into the first position, thus blocking further rotation of the rotatable part 1A. For this purpose, a spring 12 is provided which forces the blocking device 9 downwards into recess 11 and against catch 10.

According to the depicted embodiment, the rotatable part 1A comprises two recesses 11, one of which is hidden by the rotatable part 1A in the figure. Thus, the blocking device can, after a rotation of e.g. 180 degrees, "fall" (or be forced by a second spring) into said second recess 11 which houses another catch 10 (not visible).

Figure 3:
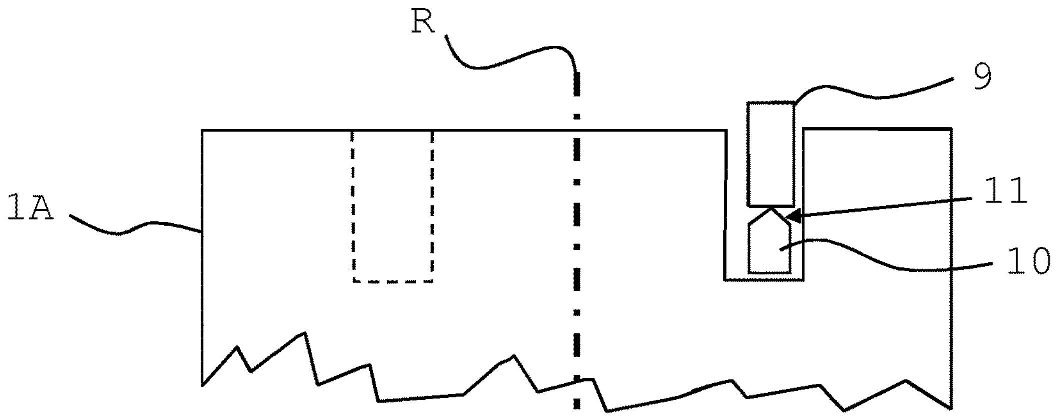
FIGS. 3-5 show different situations with regard to the position of the blocking device.
Figure 4:
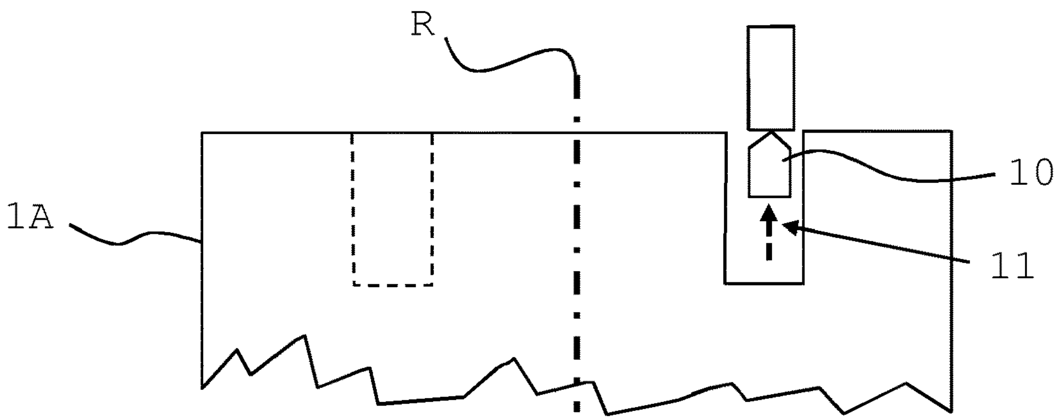
Figure 5:
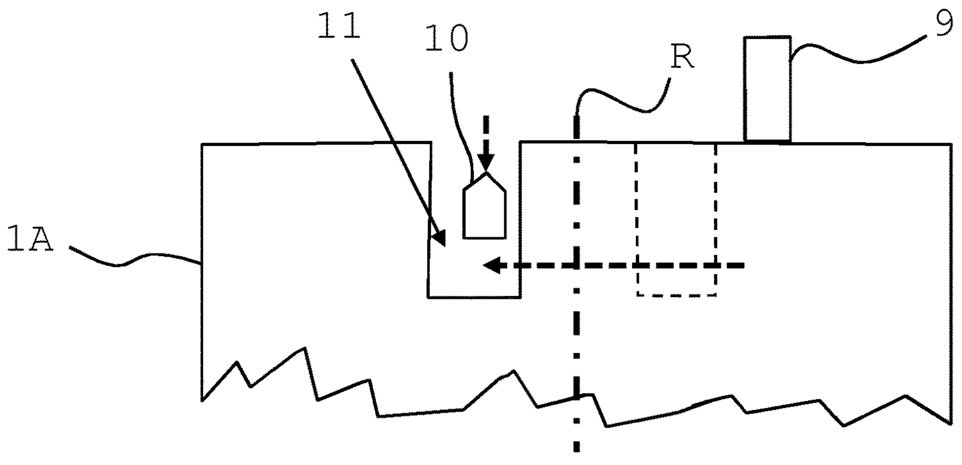

In FIGS. 3-5, different situations with regard to the position of the blocking device and the rotation angle are shown.

In FIG. 3, blocking device 9 is, to a large extent, received by a first recess 11 of rotatable part 1A. A symmetrically arranged second recess, hidden behind the front side of rotatable part 1A, is drawn in dashed lines. Catch 10 and blocking device 9 are in a respective first position, wherein rotational movement (to the right and the left in the picture) of rotatable part 1A is almost entirely inhibited, since such motion is blocked by blocking device 9 due to its radial immobility.

According to FIG. 4, catch 11 has pushed blocking device 10 out of recess 11 (dashed arrow). Now, both parts are in their respective second positions. However, although rotation of rotatable part 1A is possible, it has not started yet.

In FIG. 5, rotatable part 1A has rotated around rotation axis R, together with catch 10 (dashed arrow). Blocking device 9 slides along the upper edge of rotatable part 1A. During rotation, catch 10 moves back from the second position towards the first position which will be reached, at the latest, when a full loading cycle (rotation of e.g. 180 degrees) is completed. Then, blocking device 9 can be received once again in a recess; in the depicted embodiment, this will be the second recess drawn in dashed lines.

LIST OF REFERENCES 1 housing
1A rotatable part
1A' co-rotatable part
1B second part
2 reservoir
3 pumping chamber
4 valve
5 riser pipe
5A interior end
5B exterior end
6 nozzle
7 means for the storage of potential energy
8 valve
9 blocking device
10 catch
11 recess
12 spring
F liquid
X break lines
R rotation axis

What is claimed is:

1. Inhalation device for medically active liquids for generation of an aerosol, comprising a housing, inside this housing a reservoir for storing a liquid, a pumping device with a pumping chamber for generation of a pressure inside said pumping chamber, wherein the pumping chamber is fluidically connected with the reservoir, a riser pipe which can be received with at least one reservoir-facing interior end in said pumping chamber, and a nozzle which is connected liquid-tight to an exterior end of the riser pipe, wherein the interior volume of the pumping chamber is changeable by means of linear relative motion of the pumping chamber to the riser pipe, and wherein said linear relative motion can be effected by a relative rotation of a rotatable part which is part of, or connected to, the housing with respect to a second part of said housing, such that said relative rotation is converted into said linear relative motion by means of a gear mechanism, and wherein a means for the storage of potential energy is provided which is chargeable by means of said relative rotation, and wherein said energy is releasable to said pumping device when released by activation of a release means, a blocking device which is adapted to block rotation of the rotatable part;

wherein the blocking device is adapted to be moveable between a blocking position and a non-blocking position, and wherein the blocking device is adapted to (a) move into the blocking position upon rotating the rotatable part by a predefined rotation angle during charging of the means for the storage of potential energy and when the means for the storage of potential energy is charged, and (b) move into the non-blocking position upon activating the release means.

2. The inhalation device according to claim 1, wherein the blocking device is radially immobile.

3. The inhalation device according to claim 1, wherein the blocking position and the non-blocking position are axial positions.

4. The inhalation device according to claim 1, wherein the blocking device, upon activation of the release means, is pushed from the blocking position to the non-blocking position by means of a catch which is fixed to and/or can move together with the pumping chamber.

5. The inhalation device according to claim 4, wherein the rotatable part has an axial recess configured to receive at least a part of the blocking device such that, when said blocking device is at least partially received in said recess, rotation of the rotatable part is blocked or nearly blocked, whereas when the blocking device is outside of said recess, the rotatable part is unblocked.

6. The inhalation device according to claim 5, wherein the circumferential dimension of the recess is larger than that of the blocking device such as to allow a restricted further rotation of the rotatable part upon the receipt of the blocking device in the recess before rotation of the rotatable part is entirely blocked.

7. The inhalation device according to claim 6, wherein said restricted further rotation corresponds to a rotation angle of not more than about 10°.

8. The inhalation device according to claim 5, wherein said catch is configured (i) to fit in, and (ii) to axially move within said recess.

9. The inhalation device according to claim 5, wherein the rotatable part comprises two recesses, and wherein the two recesses are positioned apart from each other by a rotation angle of about 180°.

10. A method for the prevention of undesired emission of medically active liquid or aerosol from an inhalation device, the inhalation device comprising a housing, inside this housing a reservoir for storing a liquid, a pumping device with a pumping chamber for generation of a pressure inside said pumping chamber, wherein the pumping chamber is fluidically connected with the reservoir, a riser pipe which can be received with at least one reservoir-facing interior end in said pumping chamber, and a nozzle which is connected liquid-tight to an exterior end of the riser pipe, wherein the interior volume of the pumping chamber is changeable by means of linear relative motion of the pumping chamber to the riser pipe, wherein said linear relative motion is effected by a relative rotation of a rotatable part which is part of or connected to the housing with respect to a second part of said housing, and wherein a means for the storage of potential energy is provided which is loaded by means of said relative rotation, and which releases said energy to said pumping mechanism when released by activating a release means, wherein (i) activating of the release means and/or release of the means for the storage of potential energy during rotating the rotatable part while loading of the means for the storage of potential energy is blocked.

11. The method according to claim 10, wherein for said blocking, a blocking device is provided.

12. The method according to claim 11, wherein the blocking device moves from a first position in which it blocks the rotation of the rotatable part to a second position in which it unblocks rotation of said rotatable part.

13. The method according to claim 11, wherein, after rotating the rotatable part for a predefined angle, thus reloading the inhalation device for another dose, the blocking device moves back from the second position to the first position.

14. The method according to claim 12, wherein, for activation of the release means and/or release of the means for the storage of potential energy, a catch is provided that slides along an axial recess which is formed in the rotatable part, pushing the blocking device from said first position to said second position.

15. The method according to claim 10, wherein loading of the means for the storage of potential energy and/or rotating the rotatable part is blocked when the release means is activated.

16. The inhalation device according to claim 1, wherein the blocking device is adapted to interface with the rotatable part to block rotation.

17. The inhalation device according to claim 1, wherein the blocking device is adapted to directly block rotation of the rotatable part.

18. The inhalation device according to claim 1, wherein the blocking device is adapted to be moveable in an axial direction between the blocking position and the non-blocking position.

19. The method according to claim 10, wherein the blocking device interfaces with the rotatable part to effect the blocking.

20. The method according to claim 12, wherein the blocking device moves in an axial direction between the first position and the second position.

* * * * *